(12) United States Patent
Coppens et al.

(10) Patent No.: US 10,603,513 B2
(45) Date of Patent: Mar. 31, 2020

(54) PATIENT TRANSFER SUPPORT LOCATING DEVICE

(71) Applicant: QFIX SYSTEMS, LLC, Avondale, PA (US)

(72) Inventors: Daniel D. Coppens, Avondale, PA (US); David M. Rabeno, Avondale, PA (US); Richard J. Herrschaft, West Chester, PA (US); Sean F. McGrenaghan, Downingtown, PA (US)

(73) Assignee: QFIX SYSTEMS, LLC, Avondale, PA (US)

( * ) Notice: Subject to any disclaimer, the term of this patent is extended or adjusted under 35 U.S.C. 154(b) by 492 days.

(21) Appl. No.: 15/327,765

(22) PCT Filed: Jul. 22, 2015

(86) PCT No.: PCT/US2015/041586
§ 371 (c)(1),
(2) Date: Jan. 20, 2017

(87) PCT Pub. No.: WO2016/014695
PCT Pub. Date: Jan. 28, 2016

(65) Prior Publication Data
US 2017/0197095 A1    Jul. 13, 2017

Related U.S. Application Data

(60) Provisional application No. 62/027,284, filed on Jul. 22, 2014.

(51) Int. Cl.
*A47C 21/06* (2006.01)
*A61N 5/10* (2006.01)
(Continued)

(52) U.S. Cl.
CPC .......... *A61N 5/1049* (2013.01); *A61B 5/0555* (2013.01); *A61B 5/704* (2013.01);
(Continued)

(58) Field of Classification Search
CPC ....................................................... A47C 21/06
(Continued)

(56) References Cited

U.S. PATENT DOCUMENTS 5,806,116 A    9/1998 Oliver et al.
6,640,364 B1   11/2003 Josephson et al.
(Continued)

FOREIGN PATENT DOCUMENTS

WO    2011139062 A2    11/2011

OTHER PUBLICATIONS

European Communication for European Application No. 15 750 858.1, dated Dec. 20, 2018, 14 pages.
(Continued)

*Primary Examiner* — Fredrick C Conley
(74) *Attorney, Agent, or Firm* — RatnerPrestia

(57) ABSTRACT

A patient transfer system is provided to move a patient between modalities. The system includes a deploying modality having a top surface configured to support the patient; a patient transfer support positionable on the top surface of the deploying modality, the patient transfer support also being configured for movement from the top surface of the deploying modality to a top surface of the receiving modality; a patient transfer support locating feature positionable to limit movement of the patient transfer support relative to the top surface of the receiving modality; and a keying feature positionable to engage at least one of a surface associated with the receiving modality or a surface of the patient transfer support, the keying feature being configured to inhibit movement of the patient transfer sup- (Continued)

port in at least one direction relative to the top surface of the receiving modality. The patient transfer support locating feature limits the range of movement of the patient transfer support relative to the top surface of the receiving modality when the patient transfer support is moved from the top surface of the deploying modality to the top surface of the receiving modality.

22 Claims, 15 Drawing Sheets

(51) Int. Cl.
    *A61B 6/04*     (2006.01)
    *A61B 5/055*     (2006.01)
    *A61B 5/00*     (2006.01)
    *A61G 7/10*     (2006.01)

(52) U.S. Cl.
    CPC .......... *A61B 6/0442* (2013.01); *A61G 7/1021* (2013.01); *A61G 7/1028* (2013.01); *A61N 2005/1063* (2013.01)

(58) Field of Classification Search
    USPC ................................................ 5/81.1 R, 84.1
    See application file for complete search history.

(56) References Cited

U.S. PATENT DOCUMENTS

| | | |
|---|---|---|
| 2002/0095722 A1 | 7/2002 | Korver, II et al. |
| 2004/0133980 A1 | 7/2004 | Coppens et al. |
| 2008/0031414 A1* | 2/2008 | Coppens .................. A61B 6/04 378/65 |
| 2009/0307839 A1 | 12/2009 | Wilson et al. |
| 2012/0186588 A1 | 7/2012 | Wilson et al. |
| 2013/0318707 A1 | 12/2013 | Perelman et al. |

OTHER PUBLICATIONS

International Preliminary Report on Patentability and Written Opinion for International Search Report PCT/US2015/041586, dated Jan. 24, 2017, 11 pages.

International Search Report and Written Opinion for International Application No. PCT/US2015/041586, dated Feb. 11, 2016, 16 pages.

* cited by examiner

PATIENT TRANSFER SUPPORT LOCATING DEVICE

CROSS REFERENCE TO RELATED APPLICATIONS

This application is a U.S. National Phase Application of PCT International Application PCT/US2015/041586, filed on Jul. 22, 2015, which claims the benefit of the earlier filed U.S. Provisional Application No. 62/027,284, titled "PATIENT TRANSFER SURFACE LOCATING DEVICE," filed on Jul. 22, 2014, the contents of each of the foregoing applications being incorporated by reference herein in their entireties for all purposes.

BACKGROUND OF THE INVENTION

Various treatment and imaging procedures require accurate positioning and repositioning of patients to ensure optimum results and outcomes. For example, radiation therapy requires accurate positioning and repositioning of patients in order to ensure that the radiation dose is delivered to the tumor and spares healthy tissue. A constant need exists among patient transport system manufacturers to develop patient transport systems and related systems and accessories that are cost-effective and/or include improved features/structures. Thus, a need exists for improved patient transport systems and related assemblies/accessories.

SUMMARY OF THE INVENTION

According to one aspect of the invention, a patient transfer support locating device is provided comprising a bar having a top surface and a bottom surface; at least one bottom locating feature extended below the bottom surface of the bar; at least one top locating feature extended above the top surface of the bar; wherein the at least one bottom locating feature is configured to engage an indexing feature on a treatment or imaging couch top and the at least one top locating feature is configured to engage an indexing feature on a patient transfer support.

The device may include a safety stop on the top surface of the bar configured to prevent the patient transfer support from sliding past the imaging or treatment couch top. The top locating feature may be configured to prevent the patient transfer support from sliding past the imaging or treatment couch top, and the at least one top locating feature may be configured such that the locating feature is larger nearer the bar and decreases in size further from the bar. Also, the at least one top locating feature may be a tapered pin such that the diameter of the pin is larger nearer the bar and decreases in size further from the bar. The at least one bottom locating feature may be a disc that engages a crescent-shaped indentation in the couch top.

The device may include a keying feature wherein the top locating feature is configured to locate the patient transfer support in the superior and inferior direction and the keying feature is configured to locate the patient transfer support in the lateral and medial direction. The keying feature may also be tapered.

The device may be constructed from MRI compatible materials, and it may include a first bottom locating feature and a second bottom locating feature, the first bottom locating feature having a dissimilar geometry to the second bottom locating feature.

According to another aspect of the invention, a method is provided for transferring a patient to an imaging or treatment modality. The method includes indexing a patient transfer support locating device onto an imaging or treatment modality; transferring a patient transfer support transversely to an imaging or treatment modality; and indexing the patient transfer support to the patient transfer support locating device.

According to yet another aspect of the invention, a patient transfer support locating device is provided including at least one bar adapted for placement on a couch top. The at least one bar includes at least one top locating feature extending upward with respect to the bar, the at least one top locating feature having a geometry configured to match an indexing feature on a patient transfer support, and at least one keying feature configured to restrict lateral movement of the patient transfer support when the patient transfer support is positioned on the treatment couch top; wherein the patient transfer support is indexed to the couch top when the patient transfer support is moved laterally with respect to the treatment couch top such that the patient transfer support indexing feature engages the at least one top locating feature.

The at least one bar may include at least one bottom locating feature extending downward with respect to the bar, the at least one bottom locating feature having a geometry configured to match an indexing feature on the couch top. The at least one keying feature optionally comprises a pin, and the at least one keying feature may restrict lateral movement of the patient transfer support when the at least one keying feature is inserted into a channel formed in the patient transfer support. The at least one keying feature is optionally inserted into the channel when the patient transfer support is lowered onto the at least one bar. The patient transfer support is optionally lowered onto the at least one bar upon deflation of an air bladder attached to a bottom side of the patient transfer support. The at least one keying feature may extend upward with respect to the bar. And the at least one top locating feature optionally extends upward with respect to the bar to a distance greater than the extension of the at least one keying feature, thereby permitting indexing of the patient transfer support to the treatment couch top prior to insertion of the at least one keying feature into the channel.

According to still another aspect of the invention, a method of locating a patient transfer support to a treatment couch top is provided, comprising placing a patient transfer support locating device with at least one bar on the treatment couch top; moving the patient transfer support over the treatment couch top; aligning at least one top locating feature extending upward with respect to the at least one bar to an indexing feature formed on the patient transfer support; and engaging the indexing feature on the patient transfer support with the at least one top locating feature.

The placing step may include aligning at least one bottom locating feature extending downward with respect to the at least one bar to an indexing feature formed on the treatment couch top. The method may include inserting at least one keying feature on the at least one bar into a channel formed in the patient transfer support. The inserting step may further include lowering the patient transfer support to the treatment couch top. Additionally, the inserting step may also include deflating an air bladder attached to a bottom surface of the patient transfer support, thereby lowering the channel over the at least one keying feature.

According to another aspect, the invention provides a treatment couch top including a top surface configured to receive a patient transfer support thereon, the top surface including at least one top locating feature the at least one top locating feature having a geometry configured to match an indexing feature on the patient transfer support, and at least one keying feature configured to restrict lateral movement of the patient transfer support when the patient transfer support is positioned on the treatment couch top. The patient transfer support is indexed to the treatment couch top when the patient transfer support is moved laterally with respect to the treatment couch top such that the patient transfer support indexing feature engages the at least one top locating feature, and the patient transfer support is restricted from lateral movement with respect to the treatment couch top when the at least one keying feature engages a channel formed in the patient transfer support.

The at least one top locating feature and the at least one keying feature are optionally formed on a bar on the top surface of the treatment couch top. The bar can be removably attached to the treatment couch top.

The treatment couch top can also include at least one indexing feature adapted to engage at least one bottom locating feature formed on a bottom surface of the patient transfer support. The at least one keying feature optionally engages the channel formed in the patient transfer support when an air bladder attached to a bottom surface of the patient transfer support is deflated.

According to another aspect of the invention, a patient transfer system is configured to move a patient between modalities. The system includes a deploying modality configured to be positioned adjacent a receiving modality, the deploying modality having a top surface configured to support the patient; a patient transfer support configured to support the patient, the patient transfer support being positionable on the top surface of the deploying modality, the patient transfer support also being configured for movement from the top surface of the deploying modality to a top surface of the receiving modality; a patient transfer support locating feature configured to extend upwardly relative to the top surface of the receiving modality and positionable to limit movement of the patient transfer support relative to the top surface of the receiving modality; and a keying feature extending downwardly from the patient transfer support or configured to extend upwardly relative to the top surface of the receiving modality, the keying feature being positionable to engage at least one of a surface associated with the receiving modality or a surface of the patient transfer support, the keying feature being configured to inhibit movement of the patient transfer support in at least one direction relative to the top surface of the receiving modality; wherein the patient transfer support locating feature limits the range of movement of the patient transfer support relative to the top surface of the receiving modality when the patient transfer support is moved from the top surface of the deploying modality to the top surface of the receiving modality.

The keying feature can be configured to extend upwardly from the top surface of the receiving surface and to engage a surface of the patient transfer support.

The patient transfer support optionally includes an inflatable bladder or cushion to facilitate movement of the patient transfer support relative to the top surface of the receiving modality. The keying feature can be configured to inhibit movement of the patient transfer support in the at least one direction relative to the top surface of the receiving modality when the inflatable bladder or cushion is deflated, and wherein the keying feature is not configured to engage the surface of the patient transfer support or the surface associated with the receiving modality when the inflatable bladder or cushion is inflated. The patient transfer support locating feature can be configured to extend upwardly from the top surface of the receiving modality is positionable to limit movement of the patient transfer support relative to the top surface of the receiving modality both when the inflatable bladder or cushion is inflated and deflated.

The patient transfer system can also include a patient transfer support locating device configured to be associated with the top surface of the receiving modality. The patient transfer support locating feature can extend from the patient transfer support locating device. The patient transfer support locating device can include a receiving modality locating feature positioned to limit movement of the patient transfer support locating device relative to the top surface of the receiving modality. The receiving modality locating feature extends downwardly relative to the top surface of the receiving modality.

The deploying modality can be a transport modality configured to transport the patient to the receiving modality. Also, the transport modality can be a trolley. Additionally, the receiving modality can be an image or treatment modality, and the image or treatment modality can be a couch.

The keying feature is optionally positionable to engage the surface of the patient transfer support. The patient transfer support locating feature optionally prevents movement of the patient transfer support in at least one direction relative to the top surface of the receiving modality beyond a limit.

According to another aspect, this invention provides a method of transferring a patient between modalities, the method includes positioning a patient transfer support on a top surface of a deploying modality; positioning the patient on a top surface of the patient transfer support; inflating a bladder or cushion of the patient transfer support and raising the top surface of the patient transfer support relative to the top surface of the deploying modality; moving the patient transfer support and the patient from the top surface of the deploying modality to a top surface of a receiving modality; limiting movement of the patient transfer support relative to the top surface of the receiving modality with a patient transfer support locating feature extending upwardly relative to the top surface of the receiving modality, wherein the patient transfer support locating feature limits the range of movement of the patient transfer support relative to the top surface of the receiving modality when the patient transfer support is moved from the top surface of the deploying modality to the top surface of the receiving modality; deflating the bladder or cushion of the patient transfer support, thus lowering the top surface of the patient transfer support relative to the top surface of the receiving modality; and inhibiting movement of the patient transfer support in at least one direction relative to the top surface of the receiving modality with a keying feature extending downwardly from the patient transfer support or upwardly relative to the top of the receiving modality by engaging a surface of the receiving modality or a surface of the patient transfer support with the keying feature.

The keying feature can inhibit movement of the patient transfer support in the at least one direction relative to the top surface of the receiving modality when the inflatable bladder or cushion is deflated, and the keying feature may not engage the surface of the patient transfer support or the top surface of the receiving modality when the inflatable bladder or cushion is inflated. The patient transfer support locating feature optionally limits movement of the patient transfer support relative to the top surface of the receiving modality when the inflatable bladder or cushion is inflated and the top surface of the patient transfer support is raised relative to the top surface of the receiving modality.

BRIEF DESCRIPTION OF THE DRAWINGS

FIG. 4 is a plan view of the system of

DETAILED DESCRIPTION OF THE INVENTION

Figure 1:
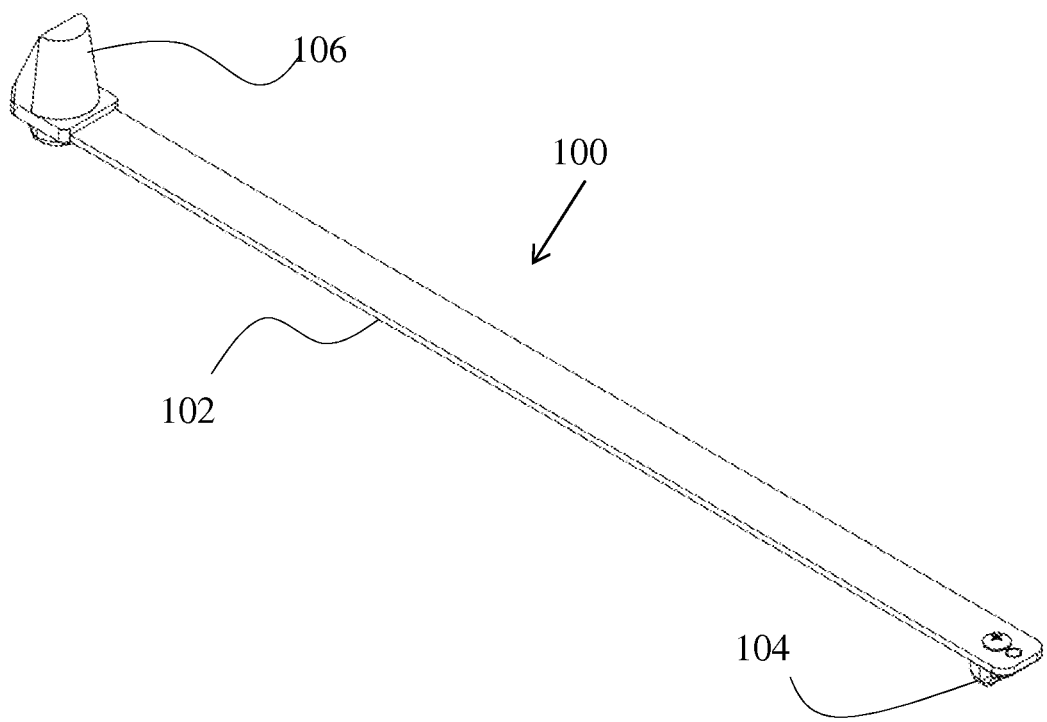
FIG. 1 is an isometric view of a patient transfer support locating device according to an embodiment of the invention.

The exemplary embodiments disclosed herein are illustrative of advantageous systems/assemblies of the present disclosure and methods/techniques thereof. It should be understood, however, that the disclosed embodiments are merely exemplary of the present disclosure, which may be embodied in various forms. Therefore, details disclosed herein with reference to exemplary patient transfer support locating devices or fabrication methods and associated processes or techniques of assembly and use are not to be interpreted as limiting, but merely as the basis for teaching one skilled in the art how to make and use the advantageous assemblies/systems and/or alternative assemblies/systems of the present disclosure.

Some equipment used today for diagnostic imaging and cancer treatment is sophisticated and expensive. To attempt to maximize the utilization of this equipment it is desirable to transport a patient to and from the equipment on a transport system/assembly which allows rapid change over from one patient to the next.

Moreover, some procedures require a rapid transition from one type of equipment to the next. More specifically, it may be desirable to transfer a patient between modalities (e.g., from a deploying modality to a receiving modality). As such, there are instances in which a patient is taken from one imaging modality (e.g., CT, PET, CT, MRI, etc.) to another or from an imaging modality to the treatment room in succession. For example, it is often desirable to perform positron emission tomography/computed tomography (PET/CT) and magnetic resonance imaging (MRI) exams in close time proximity so that the biological effect of interest can be seen in both machines. An effective patient transport system can be a significant aid in such situations.

Radiation therapy and diagnostic imaging equipment are often used in hospitals and treatment centers. Some techniques for radiation therapy and diagnostic imaging require that patients be positioned and immobilized precisely. Generally, treatment of a tumor by radiation therapy is preceded by a diagnostic imaging procedure called simulation. During simulation, the patient is positioned in the manner anticipated for treatment. This can include the physical orientation of the patient using the positioning and immobilization devices that will be used in treatment.

Furthermore, some state of the art cancer radiation therapy is increasingly based on the pinpoint application of high-energy radiation, which can be highly tailored to the shape and position of the cancerous tumor. As the size of the treatment beam decreases, the accurate location of the beam becomes much more critical. For example, if a highly tailored treatment beam is off target (e.g., by a few millimeters), it may miss the tumor. Because of these new techniques, it becomes increasingly desirable to know the location/shape of the tumor accurately when the patient is positioned for treatment.

The present disclosure provides improved patient transfer support locating devices, and related methods of use. More particularly, the present disclosure provides indexable positioning of a patient transfer support with reference to an imaging or treatment couch top. For example, the device may be used to locate a patient transfer support for diagnostic imaging (e.g., CT, MRI, PET/CT, PET/MRI) and/or radiation therapy applications (e.g., photon, proton, brachytherapy), although the present disclosure is not limited thereto. Rather, it is noted that the device of the present disclosure can be used for a wide variety of purposes/treatments/applications.

In certain embodiments, the device of the present disclosure is configured and dimensioned to be utilized with a variety of imaging and/or treatment modalities/environments. As such, the target imaging or treatment assemblies/ surfaces that the device may be used with may include many different types of equipment/surfaces (e.g., radiation therapy treatment tables/surfaces, CT tables/surfaces, MRI tables/surfaces, brachytherapy tables/surfaces, etc.).

Current practice provides that it is important that the patient be simulated in substantially the same position on the assemblies/devices as will be used in treatment to attempt to ensure accurate tumor location for treatment. Accurate tumor location and treatment spares the surrounding healthy tissue. This positioning and/or immobilization process can be extensive and time consuming. It can be beneficial, therefore, to set up the patient beforehand outside the room containing the actual treatment or imaging equipment to better utilize time on the treatment or imaging equipment. In some cases, imaging and treatment are done on the same day. In these cases it can be beneficial to set up the patient once and have them remain positioned/immobilized throughout the imaging and/or treatment procedures. When transporting patients from one piece of equipment to another it is generally desirable to employ an efficient and easy-to-use patient transfer system, as such a system can provide for the safe and efficient transfer of a patient from one target modality/surface to another. It is noted that the easy and safe transfer is beneficial for both the patient and the operator moving the patient.

In illustrative embodiments, the present disclosure provides for improved and easy-to-use locating of a patient transfer support with respect to an imaging or treatment couch top, thereby providing a significant operational, commercial and/or manufacturing advantage as a result. Moreover, by utilizing the devices of the present disclosure for imaging/treatment the users (e.g., hospitals and treatment centers) can experience improved utilization of equipment and higher patient throughput, which in turn can lower costs and provide improved/faster patient care. Furthermore, illustrative devices of the present disclosure provide that the patient can be repeatably positioned and/or immobilized precisely, thereby providing a significant clinical advantage as a result.

Furthermore, the device of the present disclosure provides for the efficient use of imaging and treatment equipment by enabling set-up of the patient on the positioning/immobilization assembly/device in a separate room, thereby leaving the treatment equipment free until needed.

The present disclosure provides devices that are configured to accurately, safely, and repeatably locate a patient transfer support for various diagnostic imaging and treatment applications/environments (e.g., diagnostic imaging, high-energy radiation therapy, image guided surgery, operating room, interventional procedures, general medical procedures, trauma and emergency medical services).

In illustrative embodiments, the patient transport systems/assemblies of the present disclosure are configured and dimensioned to be utilized with a wide variety of imaging and/or treatment modalities/environments. For example, the target treatment assemblies/surfaces that the patient may be transferred to and/or from (via the improved patient transport assemblies/systems of the present disclosure) can include many different types of equipment/surfaces (e.g., radiation therapy treatment, CT, MRI and/or brachytherapy equipment/tables/surfaces, interactive robotic surfaces, transport devices, etc.).

The present disclosure provides for the accurate, safe, and repeatable positioning of patients utilizing the indexing features of the couch top of the imaging or treatment modality such as crescent-shaped indentations on the perimeter of the couch top as described in U.S. Pat. No. 5,806,116, which is incorporated by reference herein. Although this is the most common configuration of these indexing features, the present invention can be applied to any indexing scheme known to one skilled in the art. The present disclosure illustrates embodiments including a bar that is configured to be positioned in these indexing features using at least one bottom locating feature attached to or extending from the bottom surface of the bar. The device also provides at least one top locating feature attached to or extending from the top surface of the bar which may be configure to interface with at least one indexing feature of a patient transfer support. One or more features located on the top surface of the bar may be configured to accurately and repeatedly locate the patient transfer support with respect to the couch top.

In illustrative embodiments, one or more features extending from the top surface of the bar may be configured to act as a safety stop which prevents the patient transfer support from being moved past the couch top. This feature reduces the burden on hospital staff to ensure that a patient is not injured during transfer to the imaging or treatment modality.

Referring now to the drawings, like parts are marked throughout the specification and drawings with the same reference numerals, respectively. Drawing figures are not necessarily to scale and in certain views, parts may have been exaggerated for purposes of clarity.

Referring to the figures generally, the invention provides patient transfer support locating devices, such as devices 100, 800, 900, 1200, 1300, and 1500. The locating devices may be used to locate a patient transfer support, such as surfaces 510, 1100, 1400, 2000, and 2500, to an imaging or treatment modality that can be in the form of treatment couch tops, such as couch tops 310, 730, 1000, 1508, 2300, 2400, and 2600. The locating devices generally include at least one top locating feature, such as features 106, 804, 902, 1202, 1302, and 1502, as well as at least one bottom locating feature, such as features 104, 806, 904, and 1204. The locating devices may also include at least one keying feature, such as keying features 802, 906, 1206, 1306, and 1506. The keying feature and top locating feature are optionally provided on the same or separate components of the system. For example, the locating device may include the keying feature and the top locating feature. Alternatively, the keying feature and/or the top locating feature can be provided on another surface or component associated with a modality.

The top locating features may be adapted to engage indexing features formed on the patient transfer support (e.g., indexing features 512 and 1101). Furthermore, the bottom locating features may be adapted to engage indexing features formed on the treatment couch top (e.g., features 312 and 1002). The engagement and alignment of the aforementioned locating features and indexing features allow for location of the patient transfer supports with respect to the treatment couch tops.

Additionally, the patient transport surfaces may include channels, such as channels 1102 and 1510 that are adapted to receive the keying features of the locating devices. When the keying features are inserted into the channels, the lateral and medial movement of the transfer supports with respect to the couch tops is restricted. The insertion may be accomplished by lowering the transfer supports with respect to the couch tops when the transfer supports are aligned and indexed to the couch tops. The insertion may also be accomplished by raising the keying feature into the channel of the transfer support.

Figure 2:
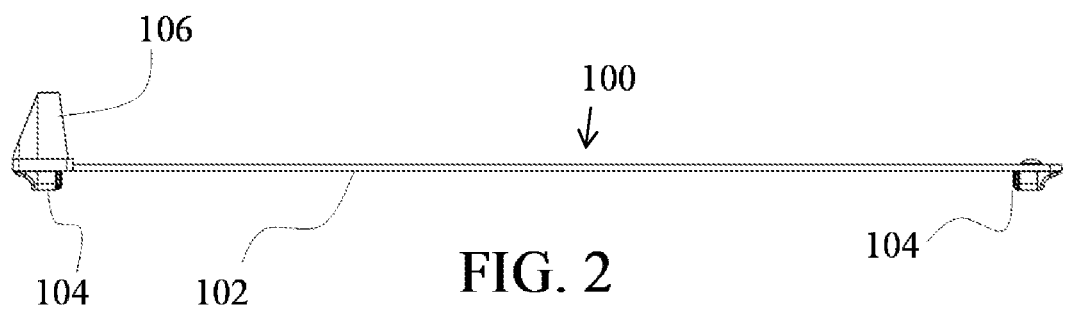
FIG. 2 is an end view of a patient transfer support locating device according to an embodiment of the invention.

With reference to FIG. 1 and FIG. 2 the patient transfer support location device 100 comprises a bar 102, at least one bottom locating feature 104 and at least one top locating feature 106. The top locating feature 106 and bottom locating feature 104 may be an integral feature of the bar 102 or may be removably or permanently attached to the bar 102. For example, the bar 102, bottom locating feature 104, and top locating feature 106 could all be machined or otherwise formed from a single piece of material. Alternatively, these could be separate pieces that are screwed, snapped, bonded together, clamped, or otherwise fastened. The bar 102 is configured to span the width of a treatment or imaging modality such as a couch top (not shown). Couch tops typically used in radiation therapy are approximately 530 mm wide. The at least one bottom locating feature 104 is configured to engage indexing features on the imaging or treatment couch top. The most common form of indexing found in radiation therapy is crescent-shaped indentations running along the sides of the couch top. The at least one bottom locating feature 104 can be configured to engage this type of indexing or any other indexing scheme which will be understood to one skilled in the art from the description herein. In one embodiment, the at least one bottom locating feature 104 is manufactured from a compliant material such that a press-fit is established between the locating feature and the indexing on the couch top. Alternatively, a cam may be used to tightly engage the locating features with the indexing features. Further, a spring biased mechanism may be used to engage the indexing features.

The top locating feature 106 is configured to engage with indexing features on a patient transfer support. These indexing features may be the same form of indexing used on the couch top or may be a different indexing configuration. In this embodiment the top locating feature 106 is tapered such that it is larger nearer the bar 102 and decreases in size as it moves away from the bar 102. This is done to make it easier for the user to engage the locating feature when transferring a patient. As shown in FIG. 1 and FIG. 2, the top locating feature 102 is configured to engage crescent-shaped indexing features. Although only one bar 102, one bottom locating feature 104 and one top locating feature 106 are depicted in FIGS. 1 and 2, it is contemplated that multiple bars and bars with multiple top and/or bottom locating features may be utilized to effectuate the invention.

Figure 3:
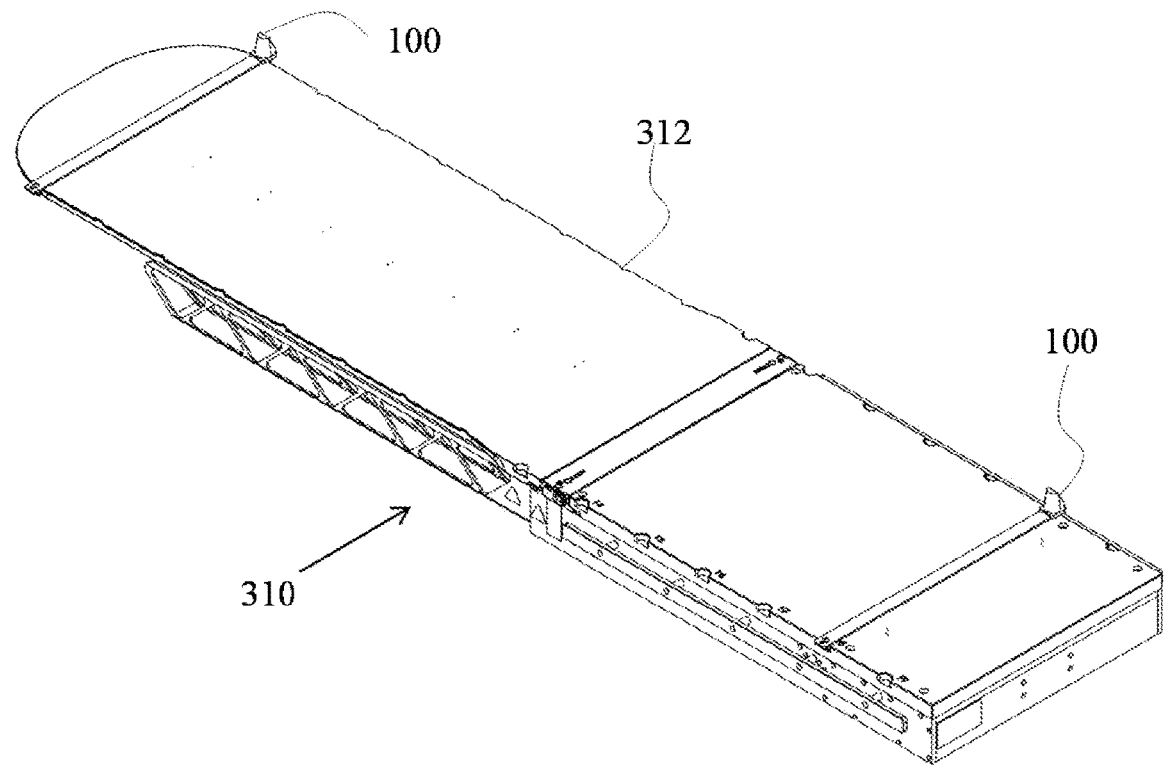
FIG. 3 is an isometric view of an embodiment of a system according to the invention including patient transfer support locating devices installed on a treatment couch top.
Figure 4:
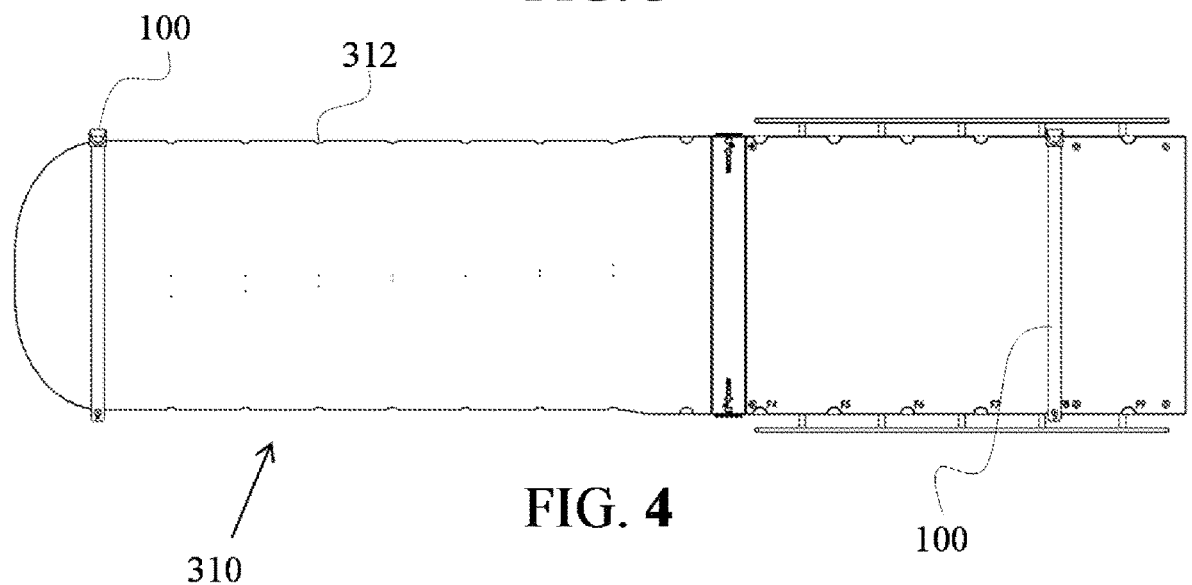

In FIG. 3 and FIG. 4 a treatment couch top 310 is shown with two patient transfer support location devices 100 in place, thus forming a patient transfer system according to an embodiment of this invention. The patient transfer support location devices are positioned using indexing features 312. The indexing features 312 on the couch top 310 are configured to match the geometry of the bottom locating features on the bar 102. As shown in the FIGS. 3 and 4, the indexing features 312 are of a crescent shape that is configured to match the geometry of the bottom locating features. Those of skill in the art will understand other suitable geometries suitable for matching indexing features with top locating features from the description herein. Any number of the patient transfer supports may be installed on a couch top 310. In a preferable configuration two of the devices 100 are used. These can be located in any of the indexing features 312 on the couch top 310. They may be spaced a sufficient distance apart to prevent rotation of a patient transfer support with respect to the couch top 310.

Figure 5:
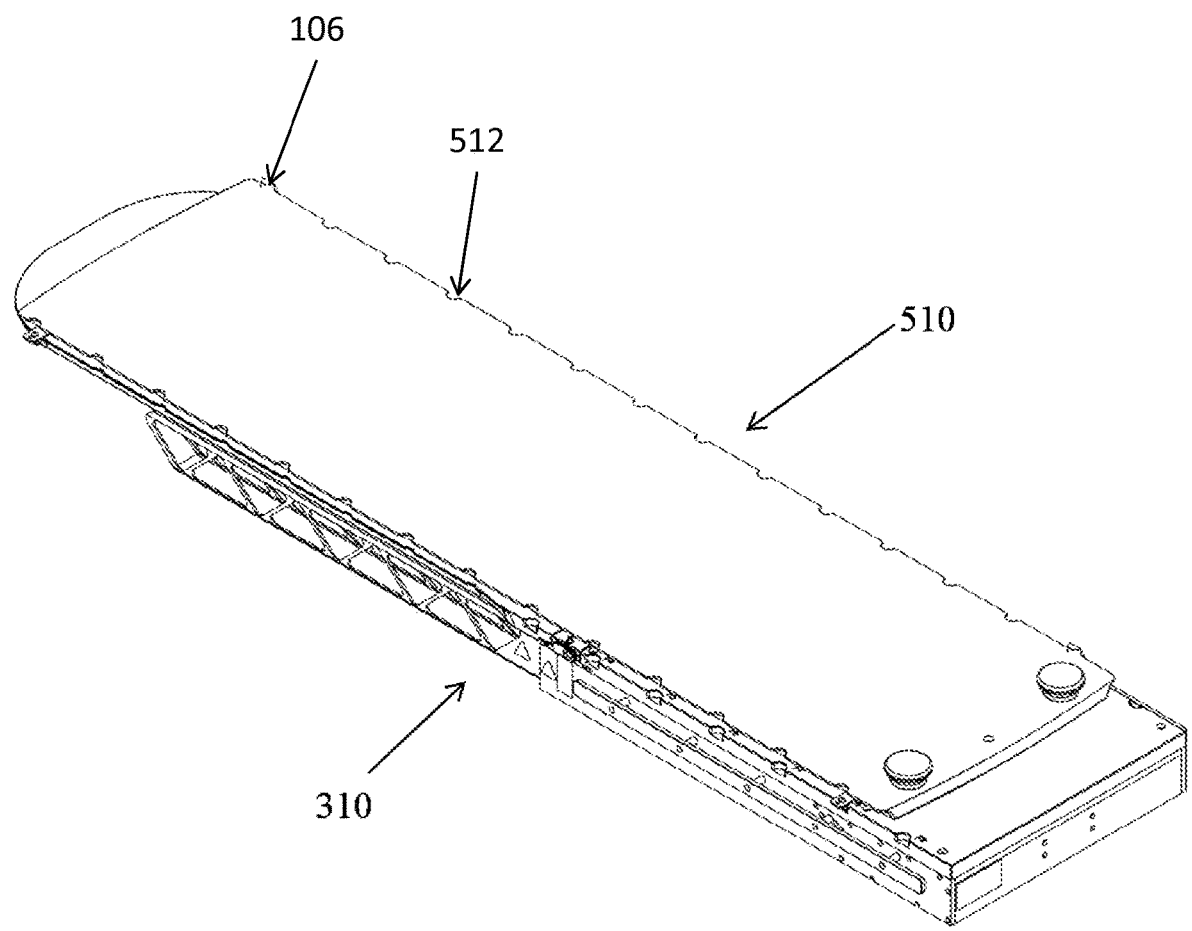
FIG. 5 including patient transfer support locating devices installed on a treatment couch top; to the invention including a patient transfer support located on a treatment couch top using patient transfer support locating devices.
Figure 6:
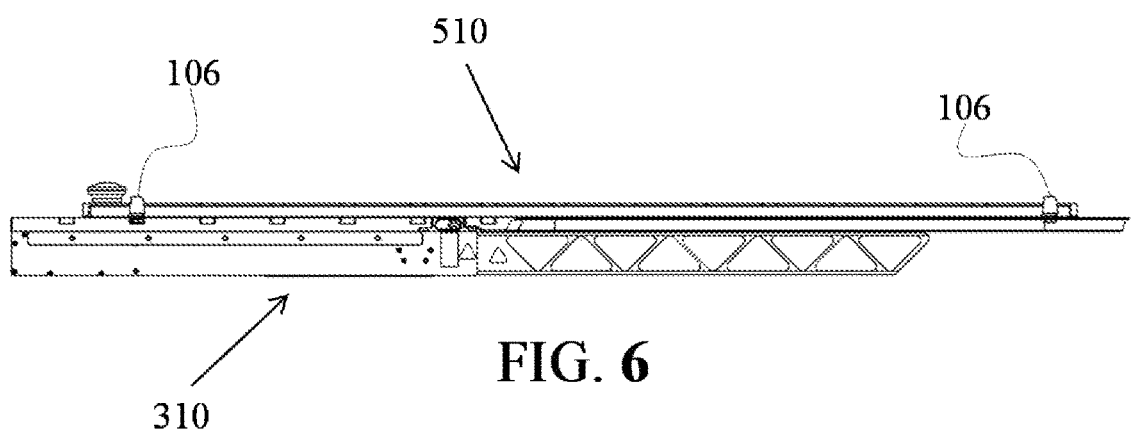
FIG. 6 is a side view of the system of FIG. 5 including a patient transfer support located on a treatment couch top using patient transfer support locating devices.

FIG. 5 and FIG. 6 show a patient transfer support 510 positioned on a treatment couch top 310, thus forming a patient transfer system according to another aspect of this invention. The indexing features 512 of the patient transfer support 510 are engaged with the top locating feature 106 of the patient transfer support locating device 100. As can be seen in these figures, the top locating features 106 can be configured to additionally serve as safety stops to prevent the patient transfer support 510 from sliding off of the couch top 310 as it is moved from left to right on the couch top 310. Alternatively, the safety stop can be accomplished with an additional feature, separate from the top locating feature 106. In order to change the configuration such that the patient transfer support 510 may be slid from the right side of the couch top 310, the patient transfer support locating devices 100 may be rotated 180 degrees with respect to the couch top.

Figure 7:
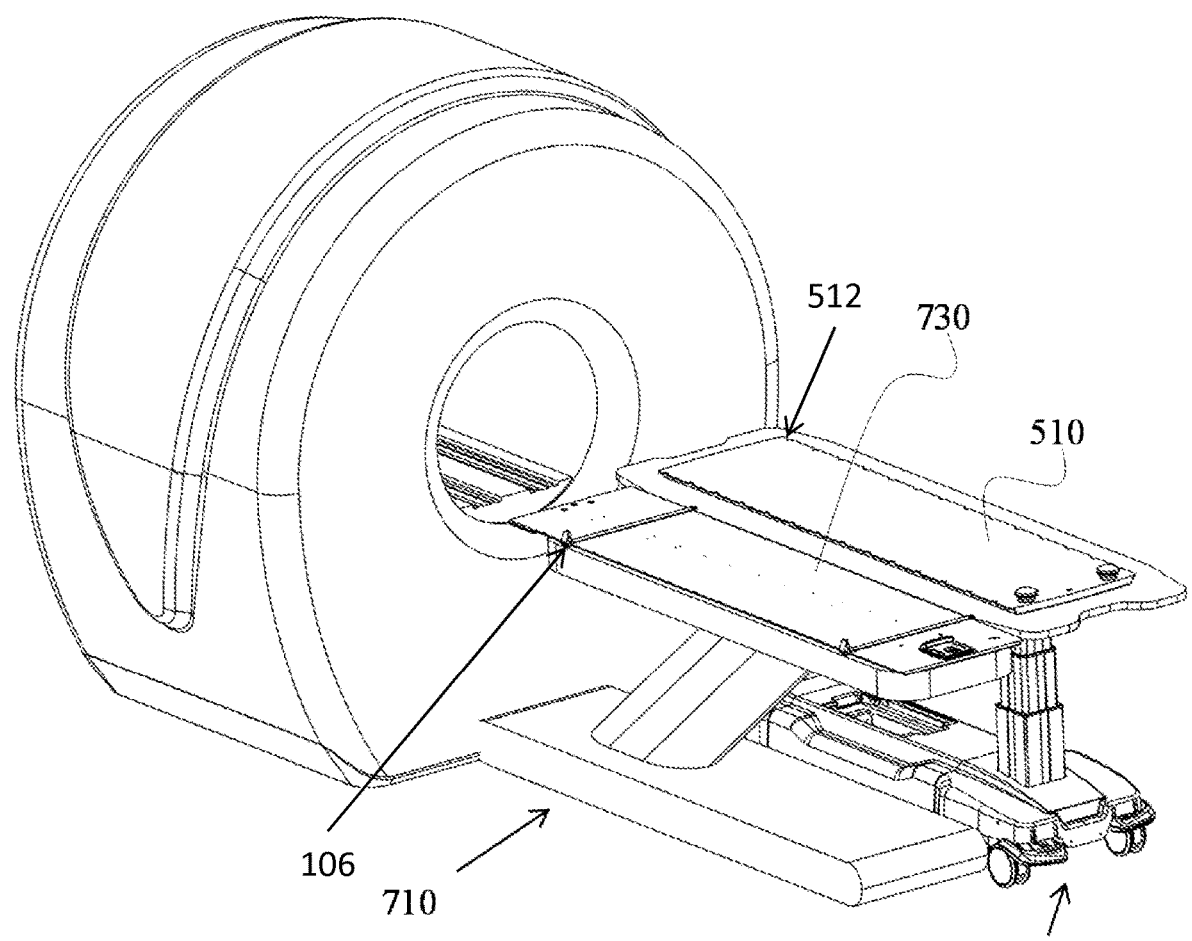
FIG. 7 is an isometric view of an embodiment of yet another system according to the invention including a patient transfer support on a trolley which is in proximity to an imaging couch top, the imaging couch top having patient transfer support locating devices installed.

With reference to FIG. 7, the present invention is shown in use on an imaging couch top 730, thus forming a patient transfer system according to another aspect of this invention. A transport modality such as trolley 720 is brought in proximity to an imaging or treatment modality such as an imaging couch top 730 which is supported by an imaging couch 710. The patient transfer support 510 is shown on the trolley 720. After the trolley 720 is placed in close proximity to the couch top 730, the patient transfer support 510 may be moved from the trolley 720 to the couch top 310 by sliding transverse to the long axis of the couch top 730. As the patient transfer support 510 is moved laterally the indexing feature 512 will come into contact with the top locating feature 106 of the patient transfer support locating device 100 which is aligned to the corresponding indexing feature 512. This will locate the patient transfer support 510 with respect to the couch top 730.

Figure 8:
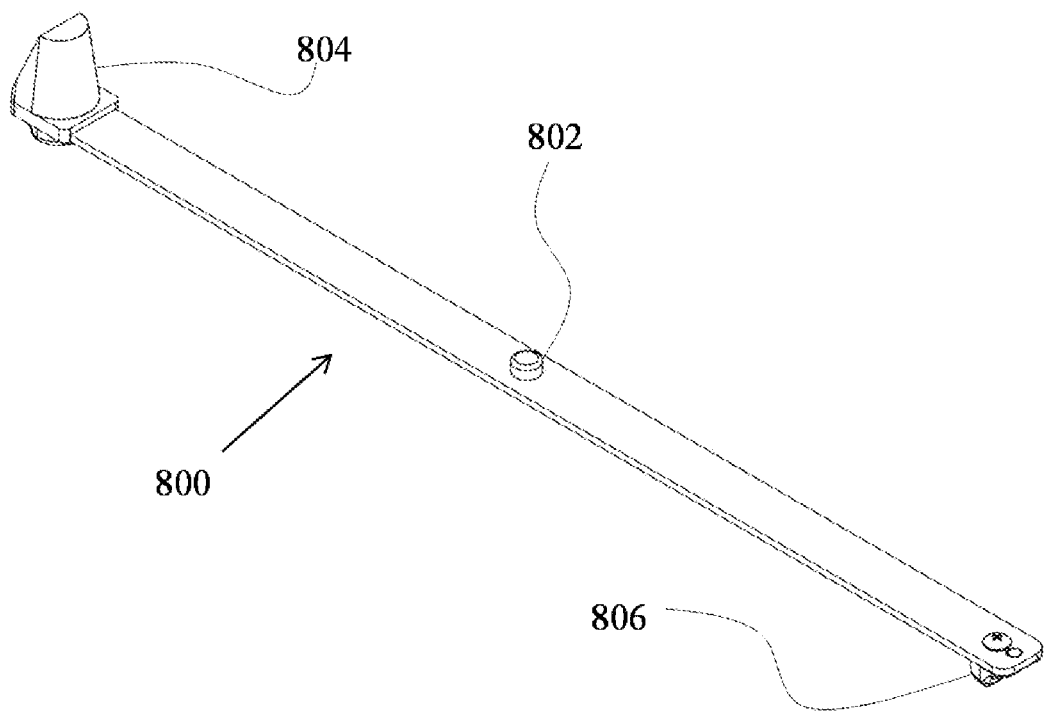
FIG. 8 is an isometric view of another embodiment of a patient transfer support locating device of the invention.
Figure 9:
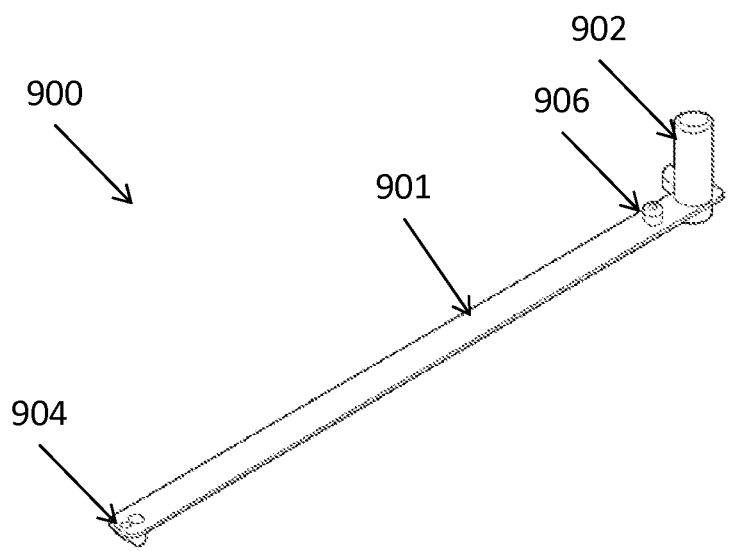
FIG. 9 is an isometric view of another embodiment of a patient transfer support locating device according to aspects of the invention.

A second embodiment of the patient transfer support locating device 800 is shown in FIG. 8. A top locating feature 804 is configured to engage with indexing features located along the perimeter of a patient transfer support. For example, the top locating feature may be configured to engage crescent-shaped indexing features as shown in previous figures. A keying feature such as a pin 802 is configured to engage a feature on the patient transfer support. For example, a channel (not shown) can be located in or on the bottom surface of the patient transfer support to engage the keying feature 802. This channel can be oriented with the axis of the channel substantially parallel to the long axis of the patient transfer support. In this way the top locating feature 804 locates the patient transfer support in the longitudinal axis (superior/inferior direction) and the keying feature 802 locates the patient transfer support in the transverse axis (medial/lateral direction). The keying feature 802 shown in FIG. 8 is a round pin but can be any shape that effectively locates the patient transfer support. FIG. 8 shows the keying feature 802 in the center of the bar but it may be located anywhere along the bar.

FIGS. 9-12 depict another embodiment of a patient transport locating device 900. The locating device 900 includes a bar 901, a top locating feature 902, a bottom locating feature 904, and a keying feature 906. The top locating feature 902 and the keying feature 906 extend upward with respect to the bar 901, while the bottom locating feature 904 extends downward with respect to the bar 901. In this embodiment, the keying feature 906 is positioned closer to the top locating feature 902 along the bar 901. The keying feature 906 is depicted as a cylindrical pin. However, other suitable keying features will be understood by those of skill in the art from the description herein.

Figure 10:
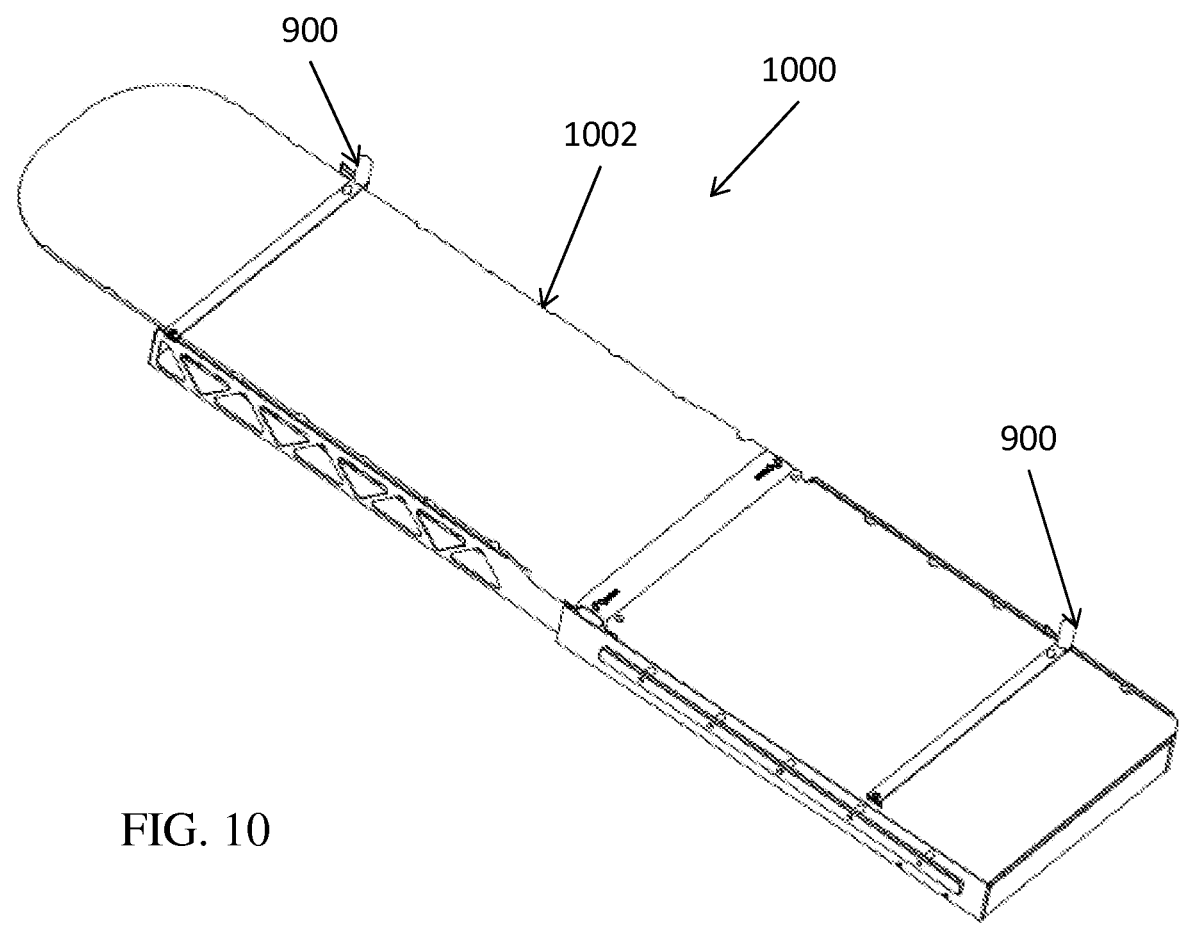
FIG. 10 is an isometric view of an embodiment of a system including a treatment couch top and patient transfer support locating devices of FIG. 9.

FIG. 10 shows a treatment couch top 1000 with the locating devices 900 positioned on the treatment couch top

1000. The treatment couch top 1000 includes indexing features 1002 similar to the indexing features described above.

Figure 11:
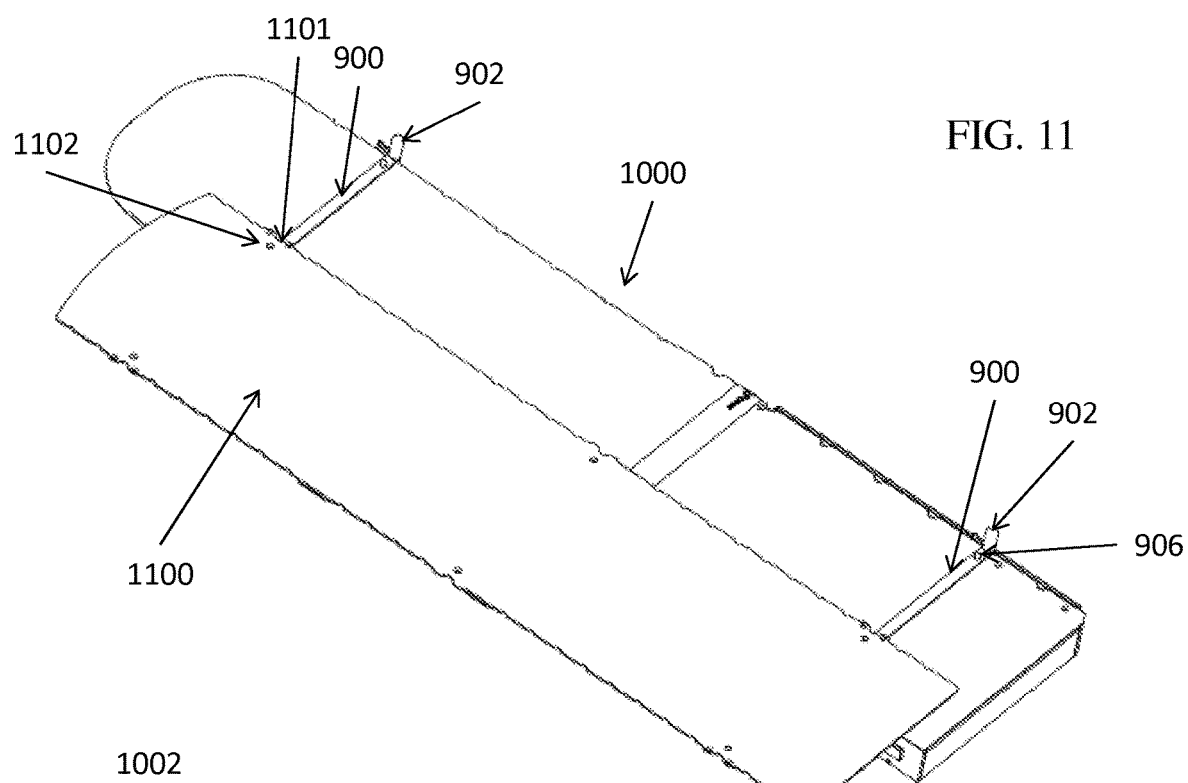
FIG. 11 and FIG. 12 depict a patient transfer support being moved with respect to a treatment couch in accordance with aspects of the invention.
Figure 12:
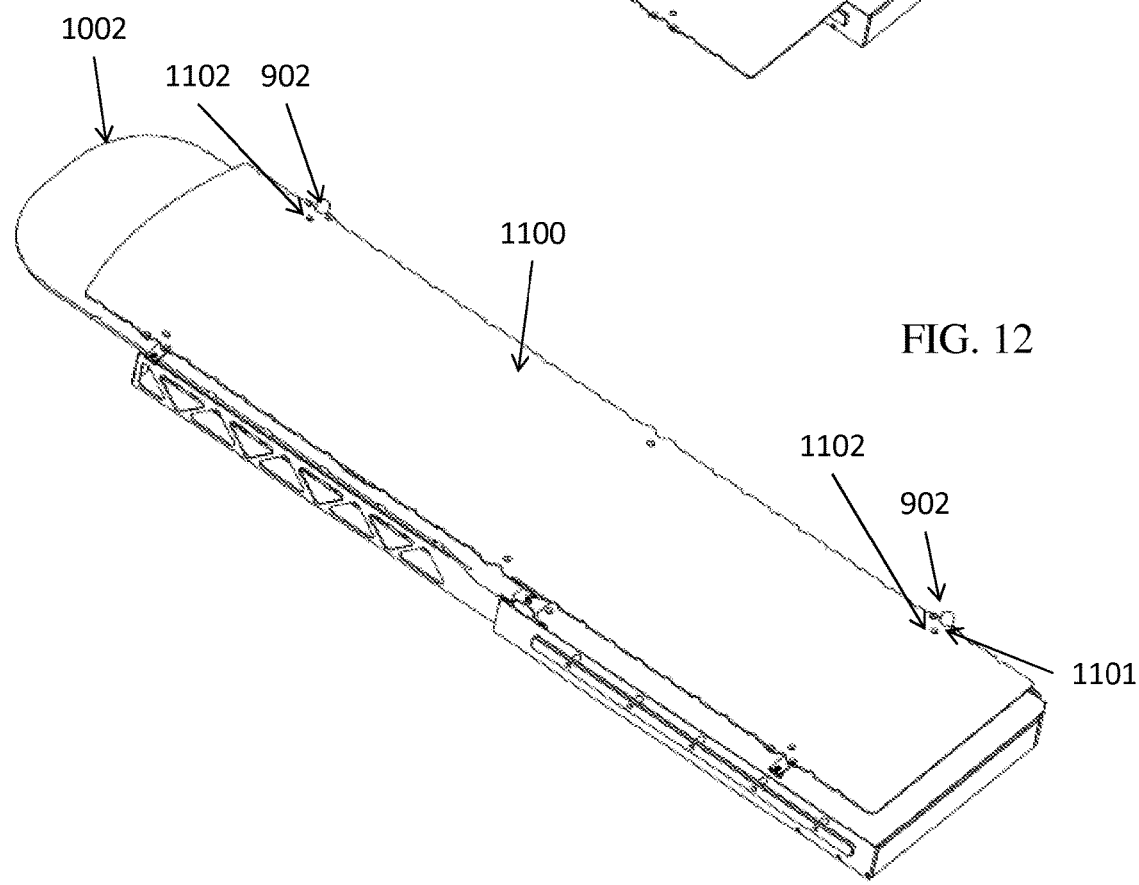

In FIG. 11 and FIG. 12, a patient transfer support 1100 is shown being positioned over the treatment couch top 1000. The patient transfer support 1100 includes indexing features 1101 formed on the patient transfer support 1100 that have a geometry to match the geometry of the top locating features 902 of the locating device 900 such that the indexing features 1101 can engage the top locating features 902. Formed on the patient transfer support 1100 are channels such as apertures or recesses 1102 that are adapted to receive the keying features 906 of the device 900. Thus, as shown in FIG. 12, when the patient transfer support 1100 is slid or moved laterally over the treatment couch top 1000, the indexing features 1101 engage the top locating features 902.

The top locating features (and/or other top locating features described herein) extend upwardly to a height that is sufficiently above the top surface of the patient transfer support such that when the patient transfer support is raised, the indexing features engage the top locating features and the patient transfer support does not get moved over or past the top locating features. In one example, the patient transfer support may be keyed to the treatment couch top by simply lowering the patient transfer support to the treatment couch top once the indexing features are engaged to the top locating features (e.g., utilizing gravity to key the surfaces without the use of clamps, vices, or other affixing mechanisms). Thus, the keying features restrict movement of the patient transfer support in the x and y directions, while gravity restricts movement of the patient transfer support in the z direction.

Figure 13:
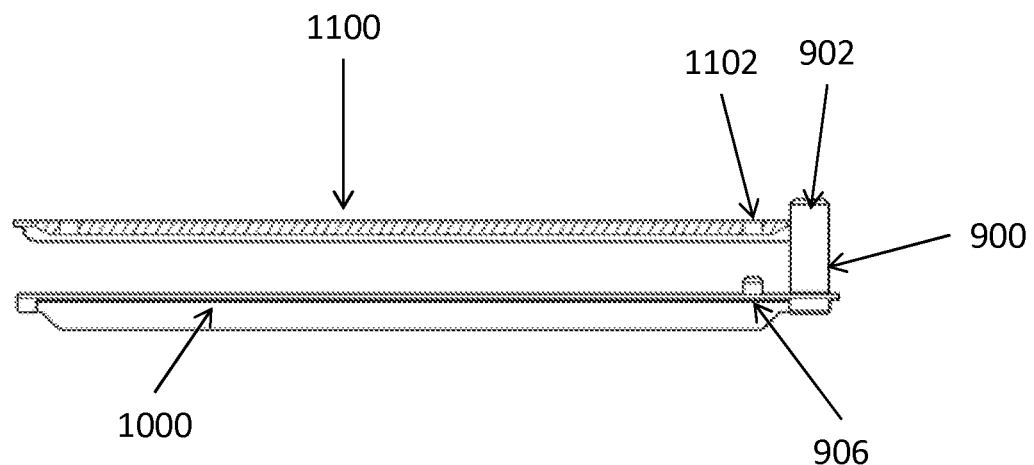
FIG. 13 and FIG. 14 are cross-sectional views showing a transfer support being lowered with respect to a treatment couch top according to aspects of the invention.
Figure 14:
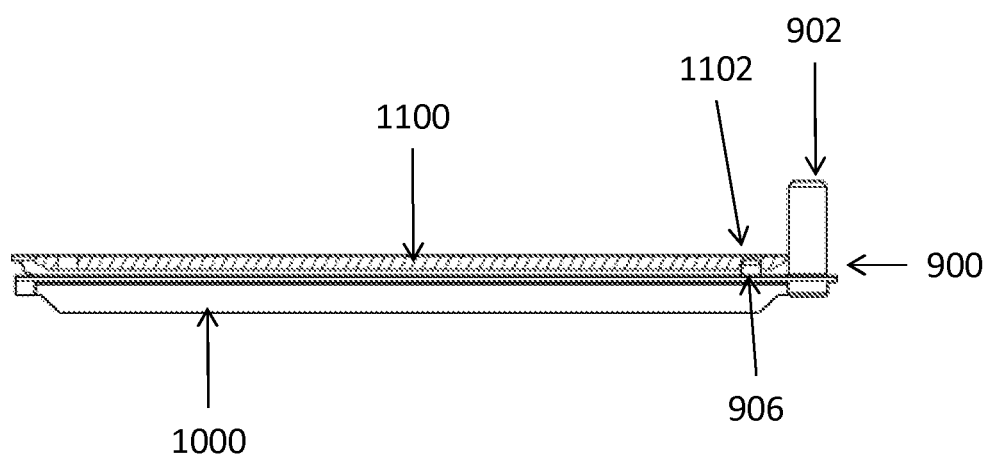

Cross sectional views of the patient transfer support 1100 being located to the treatment couch top 1000 are shown in FIGS. 13 and 14. At FIG. 13, the patient transfer support 1100 is indexed to the top locating feature 902, but is elevated with respect to the treatment couch top 1000. When the patient transfer support 1100 is lowered to the treatment couch top 1000, the keying feature 906 is inserted into the channel 1102. The insertion of the keying feature 906 into the channel 1102 restricts lateral and medial movement of the transfer support 1100 with respect to the couch top 1000.

Figure 15:
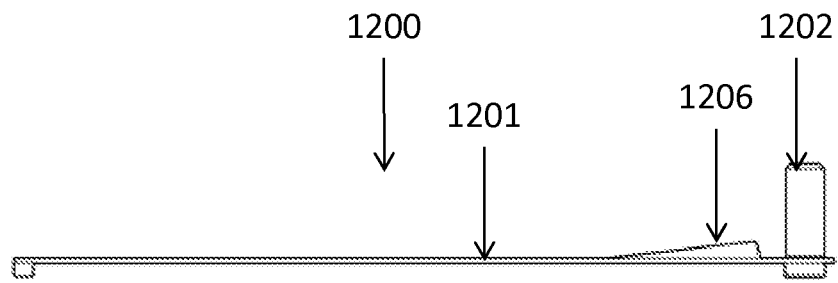
FIG. 15 and FIG. 16 are side views of additional embodiments of patient transfer support locating devices in accordance with aspects of the invention.
Figure 16:
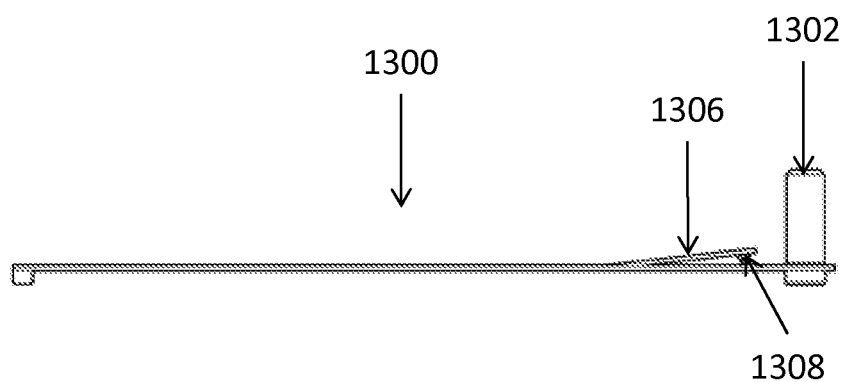

Other examples of locating devices are shown in FIGS. 15 and 16. For example, the locating device 1200 includes a keying feature 1206 that is tapered, increasing the upward extension with respect to the bar 1201 as it approaches the top locating feature 1202. The keying feature 1206 is positioned closer to the top locating feature 1202 and farther from the bottom locating feature 1204. The keying feature 1206 is configured to engage an opening formed on the bottom of a patient transfer support (not shown) such that lateral movement of the patient transfer support is restricted with respect to the treatment top when the keying feature engages the opening.

A further example of a locating device is depicted at FIG. 16. The locating device 1300 includes a keying feature 1306 that is in the form of a flange biased upward by a spring 1308. As a patient transfer support is moved toward the locating feature 1302, the transfer support pushes the keying feature 1306 downward. The spring 1308 biases the keying feature 1306 upward into a channel formed on the bottom of the transfer support, thereby preventing lateral movement of the patient transfer support with respect to the treatment top.

Figure 17:
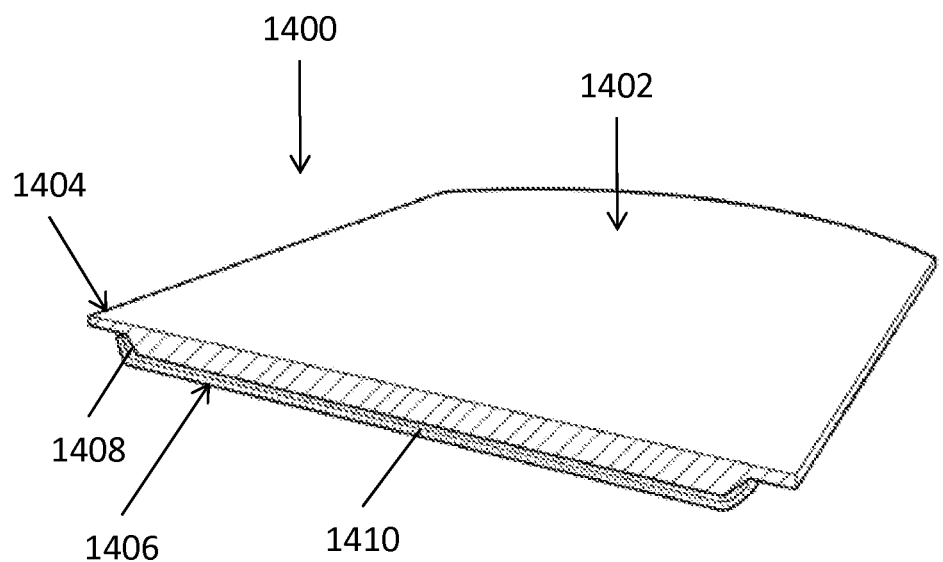
FIG. 17 and FIG. 18 are isometric cross-sectional views of an embodiment of a patient transfer support with an air bladder attached in accordance with aspects of the invention.
Figure 18:
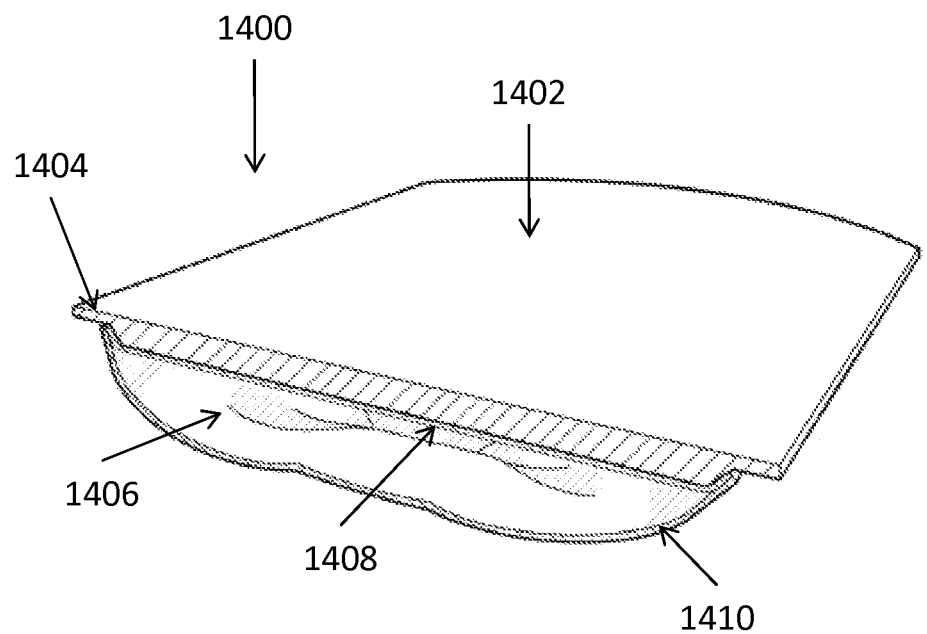

Another example of a patient transfer support 1400 is depicted in FIGS. 17 and 18. The patient transfer support 1400 includes a top surface 1402 adapted to support a patient thereon. The transfer support 1400 also includes edges 1404. Indexing features (not shown) may be formed along the edges 1404. Attached to the bottom of the transfer support 1400 is an air bladder 1406. The air bladder 1406 as depicted includes a top skin 1408 and a bottom skin 1410. As shown in FIG. 18, when the air bladder 1406 is inflated, the position of the transfer support 1400 with respect to the surface upon which it is placed is elevated. The air bladder 1406 is configured to facilitate movement of the transfer support 1400 to a couch top.

Figure 19:
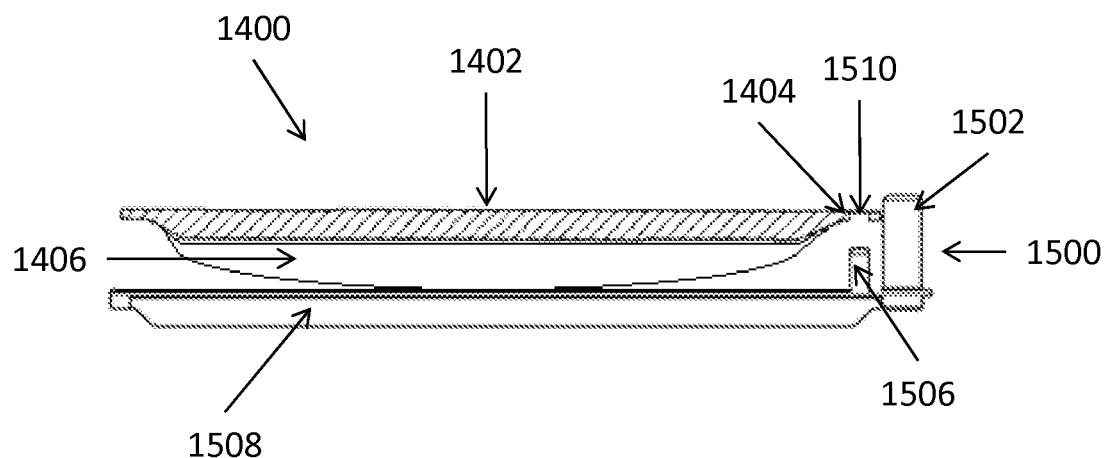
FIG. 19 and FIG. 20 are cross-sectional views of a patient transfer support with an air bladder being lowered with respect to a treatment couch top according to aspects of the invention.
Figure 20:
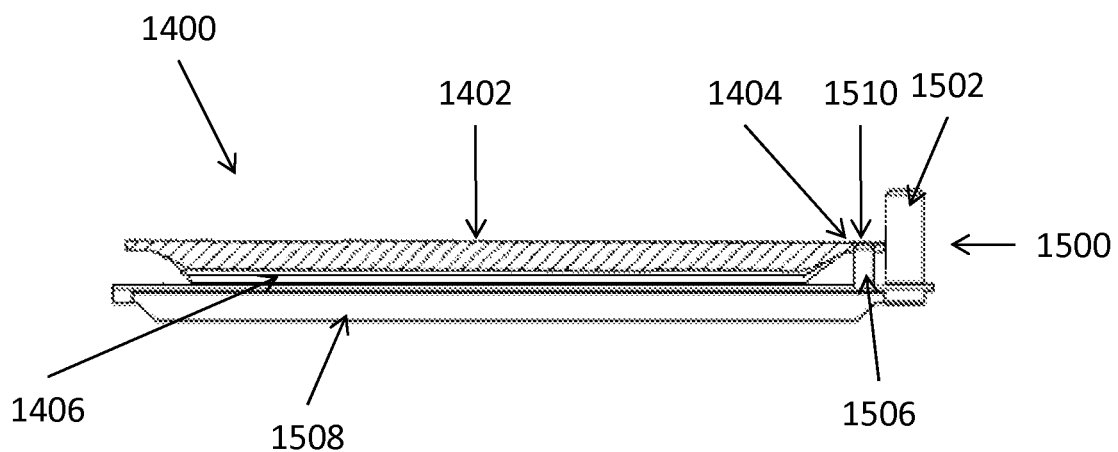

FIGS. 19 and 20 depict utilization of a keying feature with a transfer support 1400 equipped with an air bladder 1406. The transfer support 1400 is positioned over a treatment couch top 1508, and is indexed to the top locating feature 1502 of the locating device 1500. In FIG. 19, the air bladder 1406 is inflated, thereby elevating the patient transfer support 1400 with respect to the treatment couch top 1508. The indexing of the transfer support 1400 to the top locating feature 1502 aligns a channel 1510 formed near or on one of the edges 1404 of the transfer support 1400 over the keying feature 1506 of the device 1500. As shown in FIG. 20, when the air bladder 1406 is deflated, the patient transfer support 1400 approaches the treatment couch top 1508, thereby lowering the transfer support 1400 with respect to the couch top 1508. The lowering of the transfer support 1400 causes the keying feature 1506 to be inserted into the channel 1510. The insertion of the keying feature 1506 into the channel 1510 restricts lateral and medial movement of the transfer support 1400 with respect to the couch top 1508. To remove the keying feature 1506 from the channel 1510, the air bladder 1406 may be inflated, thereby elevating the transfer support 1400 with respect to the couch top 1508.

Figure 21A:
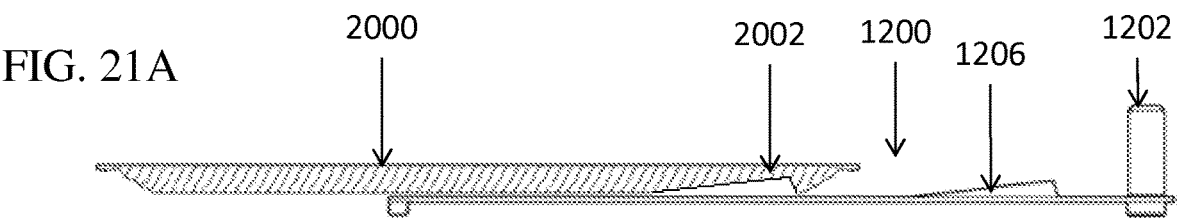
FIGS. 21A, 21B, 22A and 22B are cross-section views of a patient transfer support engaging locating devices in according to aspects of the invention.
Figure 21B:
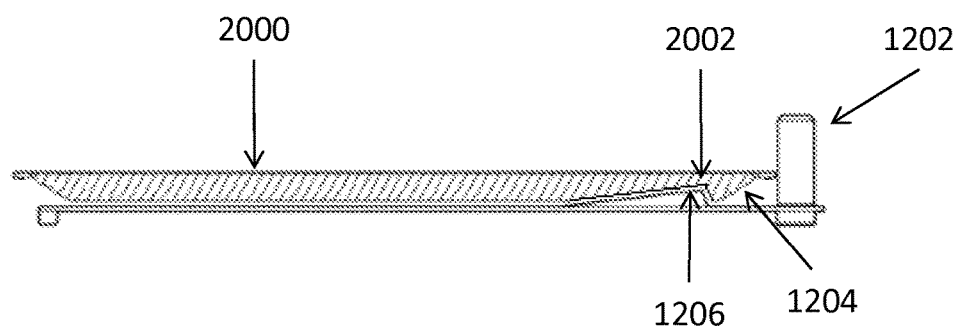

Other examples of locating a patient transfer support to a treatment couch are shown in FIGS. 21A-22B. In FIG. 21A, a patient transfer support 2000 has a channel 2002 formed on the bottom of the transfer support. As the transfer support 2000 is moved over the keying feature 1206 formed on the locating device 1200, the tapered surface of the keying feature 1206 facilitates movement of the transfer support 2000 over the keying feature 1206. Once the transfer support 2000 moves sufficiently close to the locating feature 1202, the keying feature 1206 is engaged with the channel 2002, as shown in FIG. 21B. This engagement prevents lateral movement of the transfer support 2000 with respect to a treatment surface. The keying feature 1206 may be removed from the transfer support 2000 by lifting the transfer support 2000 or by a release mechanism (not shown) that lowers the keying feature 1206 from the channel 2002.

Figure 22A:
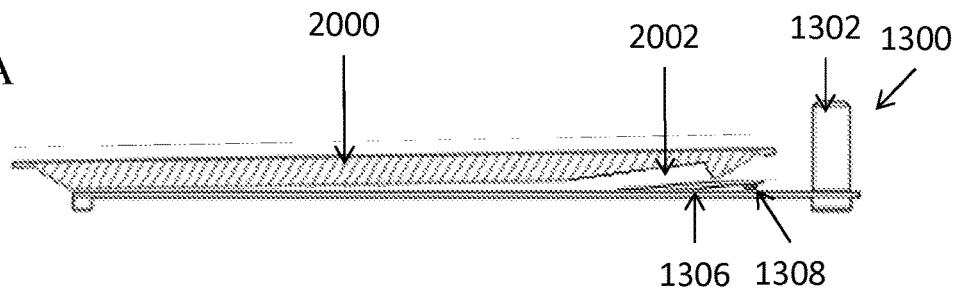
Figure 22B:
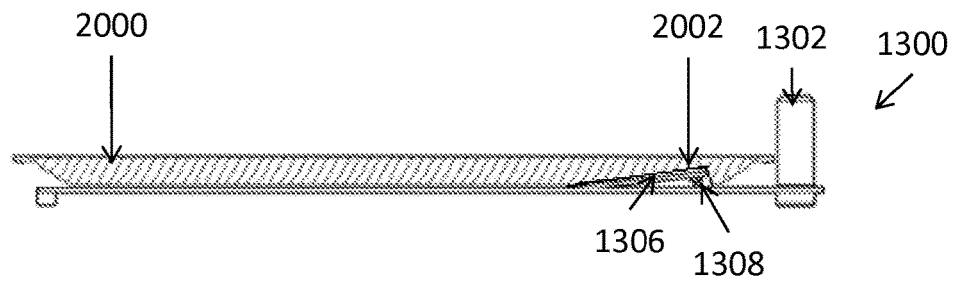

In FIG. 22A, the patient transfer support 2000 is moved on the locating device 1300 over the keying feature 1306, which is a flange type feature that is biased by a spring 1308. As the transfer support 2000 contacts the keying feature 1306, it is caused to move downward with respect to the transfer support 2000. As shown in FIG. 22B, when the transfer support 2000 is moved close enough to the locating feature 1302, the spring 1308 biases the keying feature 1306 into the channel 2002, thereby engaging the keying feature 1306 with the channel. This engagement prevents lateral movement of the transfer support 2000 with respect to a treatment top. To disengage the keying feature 1306 from the channel 2002, the transfer support 2000 may be lifted, or a release mechanism may be coupled to the keying feature 1306, which removes the keying feature 1306 from the channel.

Figure 23:
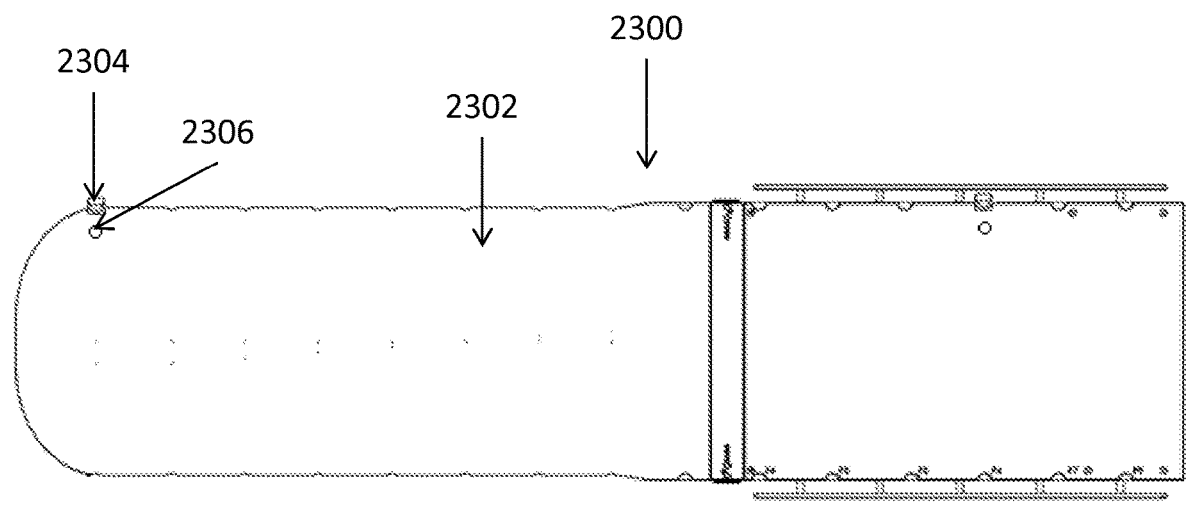
FIGS. 23 and 24 are top views of embodiments of treatment couch tops in accordance with aspects of the invention.
Figure 24:
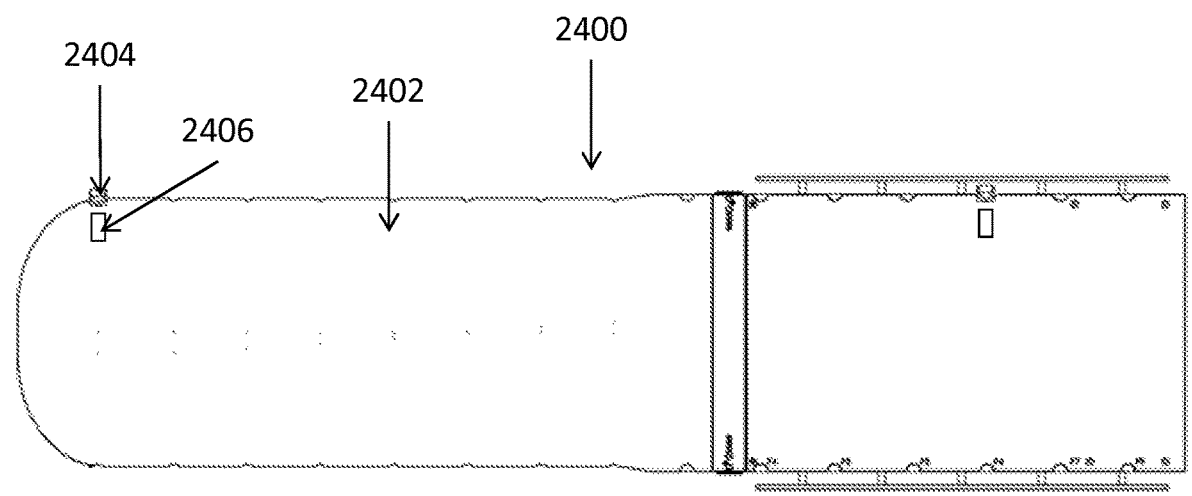

In further embodiments, keying features and locating features may be integrated directly onto the treatment couch top. As shown in FIG. 23, the top surface 2302 of the treatment top 2300 has integrated on it top locating features 2304 and keying features 2306. The keying features depicted are similar to the keying feature 906 described above. Further, in FIG. 24, the top surface 2402 of the treatment couch top 2400 has formed on it top locating features 2404 and keying features 2406. The keying features 2406 are similar to the keying features 1206 and 1306 as described above.

Figure 25:
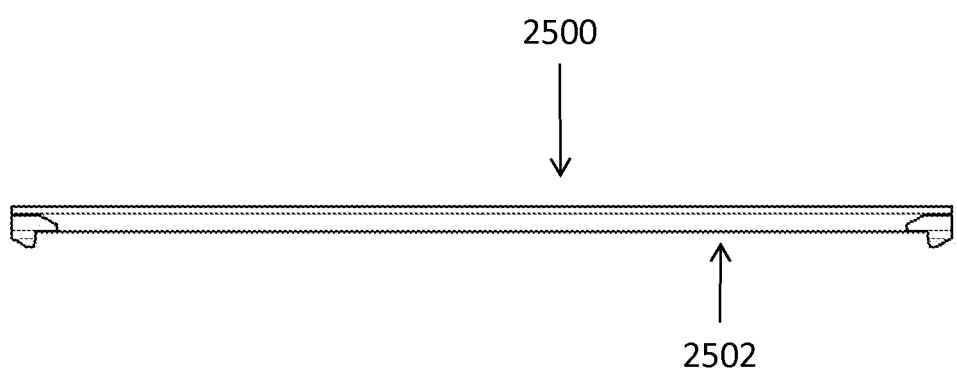
FIG. 25 is a front view of a patient transfer support according to aspects of the invention.
Figure 26:
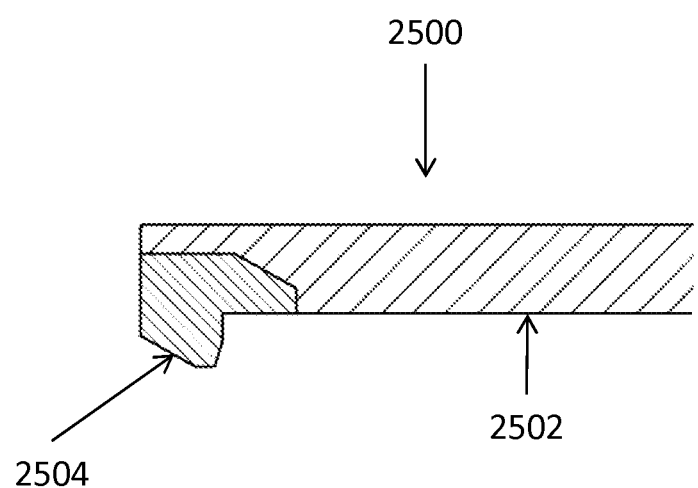
FIG. 26 is a cross-sectional view of the patient transfer support of FIG. 26.
Figure 27:
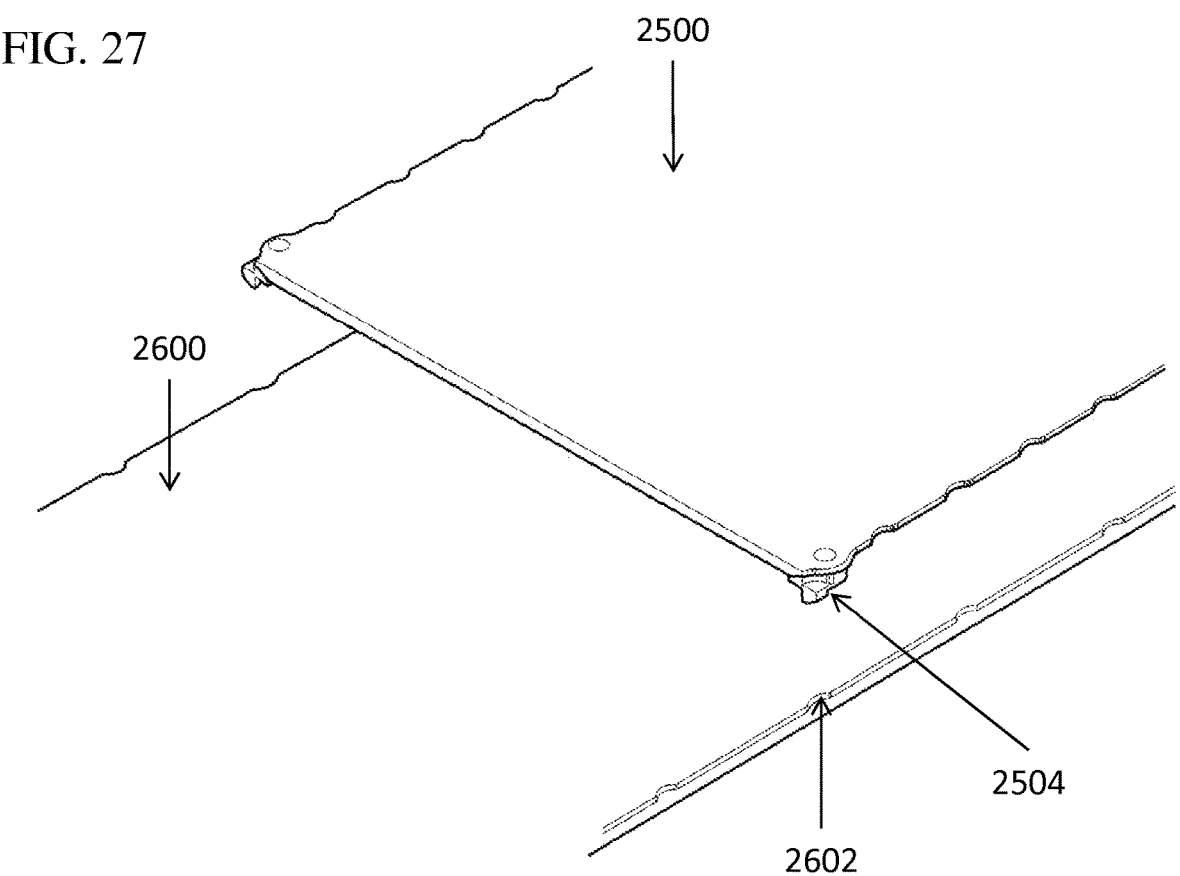
FIG. 27 is an isometric view of the patient transfer support of FIGS. 25 and 26 being moved with respect to a treatment couch top in accordance with aspects of the invention.

A further example of a system for locating a transfer support to a treatment top is shown in FIGS. 25, 26, and 27. The patient transfer support 2500 has bottom locating features (e.g., bosses) 2504 formed on the bottom surface 2502. The bottom locating features 2504 are integrated to the patient transfer support 2500. The bottom locating features 2504 are configured to engage indexing features 2602 that are formed on the treatment couch top 2600. In addition, keying features may be disposed or integrated directly on the bottom surface of the patient transfer support 2500, and may be configured to engage channels formed on the top surface of the treatment couch top 2600 when the patient transfer support 2500 is lowered to the treatment couch top 2600.

It is contemplated that various configurations may be utilized and such configurations are not limited to the examples described above. For instance, the locating features, either top or bottom locating features, may be formed on a bar removably attached to a treatment top, or may be integrated on either the transfer supports, treatment tops, or both. Similarly, the keying features and indexing features may be removable or integrated into a bar, the transfer supports, the treatment tops, etc. One of ordinary skill in the art will recognize other suitable configurations to effectuate the disclosed invention from the description herein.

Also disclosed are methods for locating a patient transfer support to a treatment couch top. The methods may include placing a locating device on a treatment couch top. The locating device may be similar to those described above. The locating devices include a bar, a top locating feature and a bottom locating feature. The locating device may be placed on the treatment couch top by aligning the bottom locating feature with indexing features on the treatment couch top.

The methods may include moving a patient transfer support over the treatment couch top. The patient transfer support may be moved laterally over the treatment couch top. The movement may be facilitated by manual pushing, by rollers, by low friction surfaces, utilization of an air bladder, and air cushion, etc.

The top locating features are aligned to an indexing feature formed on the patient transfer support. This alignment permits visual confirmation of the indexing. Once the alignment occurs, the indexing feature on the patient transfer support is engaged with the top locating feature. The engagement may be facilitated by matching geometries between the top locating feature and the indexing feature.

The aforementioned steps for locating a patient transfer support to a treatment couch top are exemplary and not exclusive. One of skill in the art will understand other suitable forming methods according to aspects of the invention from the description herein. Also, subsets of the steps may be performed, and the steps may be completed in various orders.

For example, in embodiments where an air bladder is utilized, the patient transfer support rests on a trolley or other transport modality, and is elevated upon inflation of the air bladder. Once elevated, the patient transfer support can be moved to a target modality, such as an imaging or treatment modality (e.g., a treatment couch top). Although lateral movement is described above, the patient transfer support may be moved to the target modality in various directions, including longitudinally. The transfer support is moved to the treatment couch top until it hits the top locating features, such that indexing features, if formed on the patient transfer support, engage with the top locating features. Once engaged, the air bladder is deflated, thus lowering the patient transfer support to the treatment couch top. Keying features, whether disposed on the patient transfer support or on the couch top, then are engaged and prevent at least lateral movement of the patient transfer support with respect to the treatment couch top. To disengage the keying features and thereby permit movement of the transfer support with respect to the treatment couch top, the air bladder may then be inflated, thus raising the transfer support with respect to the treatment couch and permitting movement of the patient transfer support with respect to the treatment couch top. The patient transfer support may then be moved to another target modality, such as a trolley.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

We claim:

1. A patient transfer system configured to move a patient between modalities, the system comprising:
    a deploying modality configured to be positioned adjacent a receiving modality, the deploying modality having a top surface configured to support the patient;
    a patient transfer support configured to support the patient, the patient transfer support being positionable on the top surface of the deploying modality, the patient transfer support also being configured for movement from the top surface of the deploying modality to a top surface of the receiving modality;
    a patient transfer support locating feature configured to extend upwardly relative to the top surface of the receiving modality and positionable to limit movement of the patient transfer support relative to the top surface of the receiving modality; and
    a keying feature extending downwardly from the patient transfer support or configured to extend upwardly relative to the top surface of the receiving modality, the keying feature being positionable to engage at least one of a surface associated with the receiving modality or a surface of the patient transfer support, the keying feature being configured to inhibit movement of the patient transfer support in at least one direction relative to the top surface of the receiving modality;
    wherein the patient transfer support locating feature limits the range of movement of the patient transfer support relative to the top surface of the receiving modality when the patient transfer support is moved from the top surface of the deploying modality to the top surface of the receiving modality.

2. The patient transfer system of claim 1, wherein the keying feature is configured to extend upwardly from the top surface of the receiving surface and to engage a surface of the patient transfer support.

3. The patient transfer system of claim 1, wherein the patient transfer support includes an inflatable bladder or cushion to facilitate movement of the patient transfer support relative to the top surface of the receiving modality.

4. The patient transfer system of claim 3, wherein the keying feature is configured to inhibit movement of the patient transfer support in the at least one direction relative to the top surface of the receiving modality when the inflatable bladder or cushion is deflated, and wherein the keying feature is not configured to engage the surface of the patient transfer support or the surface associated with the receiving modality when the inflatable bladder or cushion is inflated.

5. The patient transfer system of claim 3, wherein the patient transfer support locating feature configured to extend upwardly from the top surface of the receiving modality is positionable to limit movement of the patient transfer support relative to the top surface of the receiving modality both when the inflatable bladder or cushion is inflated and deflated.

6. The patient transfer system of claim 1, further comprising a patient transfer support locating device configured to be associated with the top surface of the receiving modality.

7. The patient transfer system of claim 6, the patient transfer support locating feature extending from the patient transfer support locating device.

8. The patient transfer system of claim 6, the patient transfer support locating device including a receiving modality locating feature positioned to limit movement of the patient transfer support locating device relative to the top surface of the receiving modality.

9. The patient transfer system of claim 6, wherein the receiving modality locating feature extends downwardly relative to the top surface of the receiving modality.

10. The patient transfer system of claim 1, wherein the keying feature is positionable to engage the surface of the patient transfer support.

11. The patient transfer system of claim 1, wherein the patient transfer support locating feature prevents movement of the patient transfer support in at least one direction relative to the top surface of the receiving modality beyond a limit.

12. A patient transfer support locating device, comprising:
  at least one bar adapted for placement on a couch top, the at least one bar including:
    at least one top locating feature extending upward with respect to the bar, the at least one top locating feature having a geometry configured to match an indexing feature on a patient transfer support, and
    at least one keying feature configured to restrict lateral movement of the patient transfer support when the patient transfer support is positioned on the treatment couch top;
  wherein the patient transfer support is indexed to the couch top when the patient transfer support is moved laterally or longitudinally with respect to the treatment couch top such that the patient transfer support indexing feature engages the at least one top locating feature;
  wherein the at least one keying feature restricts lateral movement of the patient transfer support when the at least one keying feature is inserted into a channel formed in the patient transfer support;
  wherein the at least one keying feature is inserted into the channel when the patient transfer support is lowered onto the at least one bar; and
  wherein the at least one keying feature is inserted into the channel when the patient transfer support is lowered onto the at least one bar upon deflation of an air bladder attached to a bottom side of the patient transfer support.

13. The locating device of claim 12, wherein the at least one bar further includes at least one bottom locating feature extending downward with respect to the bar, the at least one bottom locating feature having a geometry configured to match an indexing feature on the couch top.

14. The locating device of claim 12, wherein the at least one keying feature comprises a pin.

15. The locating device of claim 12, wherein the at least one keying feature extends upward with respect to the bar.

16. The locating device of claim 15, wherein the at least one top locating feature extends upward with respect to the bar to a distance greater than the extension of the at least one keying feature, thereby permitting indexing of the patient transfer support to the treatment couch top prior to insertion of the at least one keying feature into the channel.

17. A method of transferring a patient between modalities, the method comprising:
  positioning a patient transfer support on a top surface of a deploying modality;
  positioning the patient on a top surface of the patient transfer support;
  inflating a bladder or cushion of the patient transfer support and raising the top surface of the patient transfer support relative to the top surface of the deploying modality;
  moving the patient transfer support and the patient from the top surface of the deploying modality to a top surface of a receiving modality;
  limiting movement of the patient transfer support relative to the top surface of the receiving modality with a patient transfer support locating feature extending upwardly relative to the top surface of the receiving modality, wherein the patient transfer support locating feature limits the range of movement of the patient transfer support relative to the top surface of the receiving modality when the patient transfer support is moved from the top surface of the deploying modality to the top surface of the receiving modality;
  deflating the bladder or cushion of the patient transfer support, thus lowering the top surface of the patient transfer support relative to the top surface of the receiving modality; and
  inhibiting movement of the patient transfer support in at least one direction relative to the top surface of the receiving modality with a keying feature extending downwardly from the patient transfer support or upwardly relative to the top of the receiving modality by engaging a surface of the receiving modality or a surface of the patient transfer support with the keying feature.

18. The patient transfer method of claim 17, wherein the keying feature inhibits movement of the patient transfer support in the at least one direction relative to the top surface of the receiving modality when the inflatable bladder or cushion is deflated, and wherein the keying feature does not engage the surface of the patient transfer support or the top surface of the receiving modality when the inflatable bladder or cushion is inflated.

19. The patient transfer method of claim 17, wherein the patient transfer support locating feature limits movement of the patient transfer support relative to the top surface of the receiving modality when the inflatable bladder or cushion is inflated and the top surface of the patient transfer support is raised relative to the top surface of the receiving modality.

20. A method of locating a patient transfer support to a treatment couch top, comprising:
  placing a patient transfer support locating device with at least one bar on the treatment couch top;
  moving the patient transfer support over the treatment couch top;

aligning at least one top locating feature extending upward with respect to the at least one bar to an indexing feature formed on the patient transfer support;

engaging the indexing feature on the patient transfer support with the at least one top locating feature; and inserting at least one keying feature on the at least one bar into a channel formed in the patient transfer support;

wherein the inserting step further comprises deflating an air bladder attached to a bottom surface of the patient transfer support, thereby lowering the channel over the at least one keying feature.

21. The method of claim 20, wherein the placing step further comprises aligning at least one bottom locating feature extending downward with respect to the at least one bar to an indexing feature formed on the treatment couch top.

22. The method of claim 20, wherein the inserting step further comprises lowering the patient transfer support to the treatment couch top.

* * * * *